United States Patent [19]
Stull

[11] Patent Number: 5,417,349
[45] Date of Patent: May 23, 1995

[54] LIQUID DISPENSER FOR EYE DROPS

[76] Inventor: Gene Stull, 1 Winston Farm La., Far Hills, N.J. 07931

[21] Appl. No.: 139,141
[22] Filed: Oct. 21, 1993
[51] Int. Cl.6 ............................................. B65D 47/18
[52] U.S. Cl. ................................... 222/420; 222/562
[58] Field of Search ............... 222/420, 545, 562, 421; 604/295, 300

[56] References Cited

U.S. PATENT DOCUMENTS

| | | | |
|---|---|---|---|
| 3,409,009 | 11/1968 | Vasse | 128/249 |
| 3,872,866 | 3/1975 | Lelicoff | 128/233 |
| 3,934,590 | 1/1976 | Campagna et al. | 128/233 |
| 4,002,168 | 1/1977 | Petterson | 128/233 |
| 4,085,750 | 4/1978 | Bosshold | 128/233 |
| 4,733,802 | 3/1988 | Sheldon | 222/181 |
| 5,059,188 | 10/1991 | Goddard | 604/300 |
| 5,154,710 | 10/1992 | Williams | 604/301 |
| 5,219,101 | 6/1993 | Matkovich et al. | 222/420 X |
| 5,221,017 | 6/1993 | Cistene et al. | 222/420 X |
| 5,221,027 | 6/1993 | Gibilsco | 222/420 |
| 5,303,837 | 4/1994 | Adams et al. | 222/562 X |

FOREIGN PATENT DOCUMENTS

| | | | |
|---|---|---|---|
| 968728 | 6/1975 | Canada | 222/562 |
| 971137 | 9/1964 | United Kingdom . | |

*Primary Examiner*—Andres Kashnikow
*Assistant Examiner*—Joseph A. Kaufman
*Attorney, Agent, or Firm*—H. Gibner Lehmann; K. Gibner Lehmann

[57] ABSTRACT

A liquid dispenser for eye drops, antiseptic solutions and the like, comprises a dispensing cap having a projecting conical discharge spout with tapered side walls and an annular end wall that surrounds the orifice. Projections in the form of ribs are provided on the exposed surfaces of the spout, to minimize the likelihood of contamination of broad spout surfaces if the spout inadvertently comes in contact with exterior objects. The projections are on both the end and the side surfaces of the spout.

18 Claims, 1 Drawing Sheet

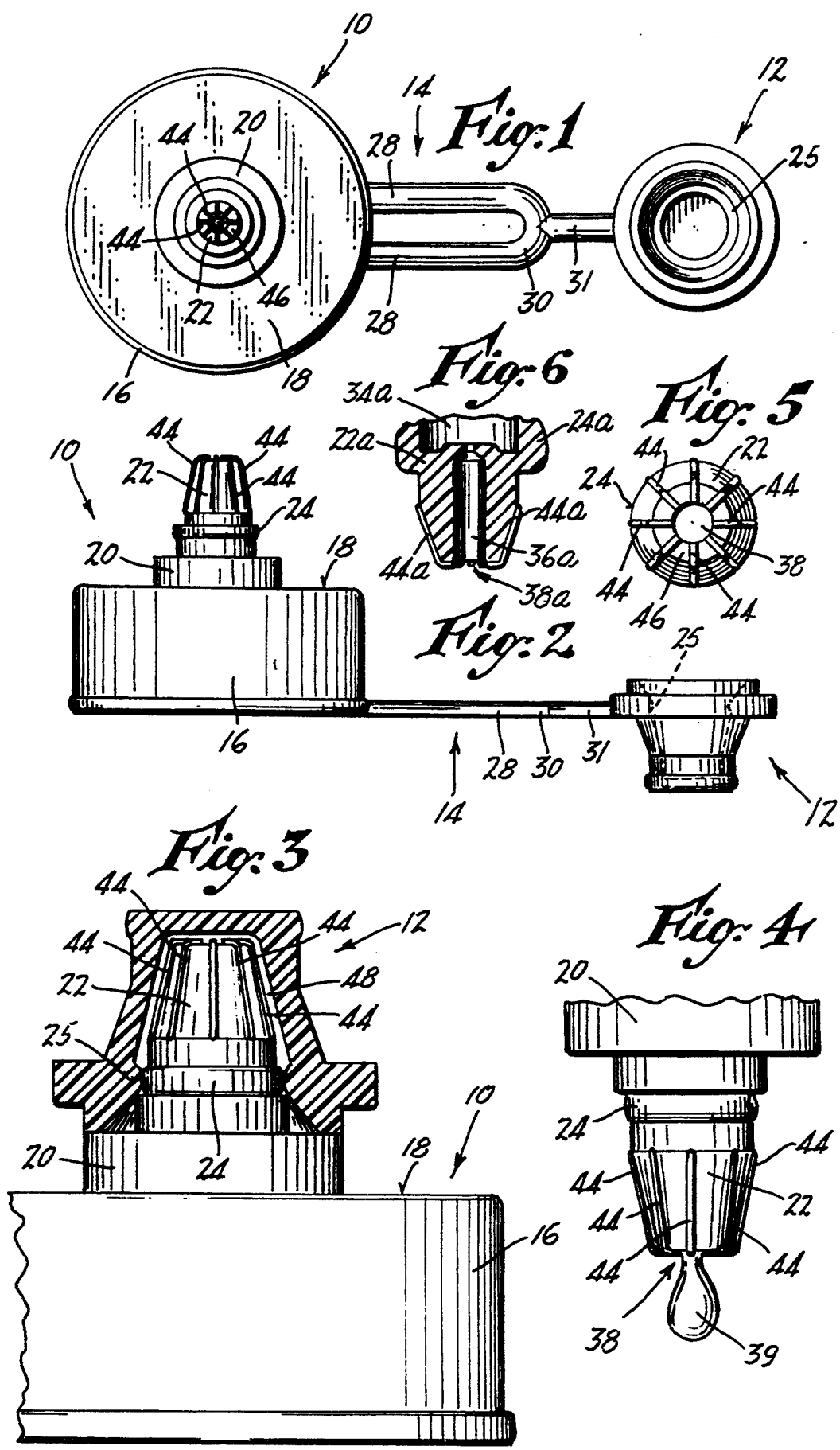

LIQUID DISPENSER FOR EYE DROPS

BACKGROUND OF THE INVENTION

1. Field of the Invention

This invention relates generally to liquid dispensers, and more particularly to dispensers of the type intended for ophthalmic applications.

2. Description of the Related Art Including Information Disclosed Under 37 CFR §§1.97–1.98

The following patents are cited as being of interest, and together with the citations made against each, as well as the patents noted in some of the respective preambles, are considered to be a sampling of prior, known dispenser constructions of the kind typically used in the field of ophthalmology.

U.S. Patents Nos.: 3,409,009, 3,872,866, 3,934,590, 4,002,168, 4,085,750, 4,733,802, 5,154,710, 5,221,027 British Patent No. 971,137.

With specific reference to the above identified 9 patents, U.S. Pat. No. 5,221,027, discloses a shield member for an eye dropper nozzle, to minimize possible damage thereto and contamination thereof. In the embodiment of FIG. 7, a semicircular shield is employed, supported by two upstanding fingers. A cup-like shield is shown in FIG. 2, whereas a shield comprising multiple upstanding fingers is illustrated in FIG. 3.

U.S. Pat. No. 4,002,168 discloses a variety of guard constructions for ophthalmic containers, mostly in the form of ring structures which perform a double function, namely positioning the container over the eye during application, and minimizing inadvertent contact with the container nozzle, and resultant contamination.

U.S. Pat. No. 3,409,009 discloses a dispenser with integral eye cup, and a metering valve for controlling the quantity of liquid discharged.

U.S. Pat. No. 4,733,802 shows a dispenser system which utilizes a spacer cup for positioning the container over the eye, and which cup has a finger notch to facilitate pulling one eyelid away, thus exposing the eyeball directly to receive the intended medicinal product.

U.S. Pat. No. 5,154,710 involves multiple dispenser constructions having various forms of spacer cups that position the dispenser over the eye of the user.

U.S. Pat. Nos. 3,872,866 and 3,934,590 illustrate dispensers employing support sleeves or collars having projecting fingers, to facilitate positioning in anticipation of the application of eyedrops.

U.S. Pat. No. 4,085,750 shows an attachment for a container wherein spring fingers on the attachment purportedly assist the user in spreading the (upper and lower) eyelids just prior to application of the eyedrops.

British Patent No. 971,137 discloses several forms of spacer guards for a bottle. In FIGS. 1 and 2, for example, there is provided a single piece guard comprising a bridge for supporting the bottle. FIG. 3 illustrates a design wherein the bottle is nestable in the bridge, for storage purposes. FIGS. 7–9 show a pair of pivoted arms which operate to position the bottle for application of drops to the eye of a user.

While the problem of product integrity is always of concern in the container field, this is especially so in the case of ophthalmic solutions and medicaments, for the reason that inadvertent contamination can lead to serious problems of eye infection and/or inflammation. Due to the proximity of the eye to the brain and to the multiple sinus cavities in and around the nose, it is incumbent upon both the pharmaceutical manufacturer as well as the consumer, to exercise the utmost care in preserving the antiseptic condition of eye solutions.

An existing closure cap construction currently in use is of a type having a base cap with screw threads that enable the base cap to be screwed onto the threaded neck of a plastic squeeze bottle, and a convergent upstanding spout on the base cap, with a small opening at the crest of the spout. A closure cap is provided, adapted to snap over the spout. An elongate integral web attaches the closure cap to the base cap, which facilitates use by the consumer, and also serves the important function of keeping the closure cap captive on the base cap, as opposed to a construction where the closure cap is completely removed and placed on a contaminated surface such as a table or sink.

One of the problems with the construction just described is that in use, the consumer lifts the closure cap with the tip of his finger, to pry it off the base cap. If care is not exercised, the likelihood exists of the tip of the finger inadvertently rubbing past the opening of the spout, thereby contaminating the adjacent surface, and possibly any residual liquid that may have collected around the spout and which has been retained thereon, by capillarity.

The problem is compounded in that the consumer does not become aware of the potential contamination when he initially grasps the dispenser because the closure cap hides or conceals the discharge opening. By the time that the consumer has pried the closure cap off, he may already have inadvertently brushed against the spout.

Use of mild chemical means (preservatives) to neutralize bacteria in such eye solutions, though frequently practiced, has not met with wide acceptance. Such chemical means are expensive, and can possibly interfere with the intended action of the eye solution and thus thwart the therapeutic effect; alternately, chemicals of the type noted can become unstable, especially over periods of several months. Their intended effect can thus be jeopardized under such circumstances.

Several manufacturers have resorted to the use of special filter screens, employing typically a pore size of 0.4 microns, and where the filter is treated with a bacteriostatic medium such as silver. Special valve structures have been devised, by which air drawn into a squeeze bottle immediately following dispensing, are channelled through a normally-closed, combined valve-and-filter unit.

Prior experience has dictated that maintaining sterility is best accomplished through time-tested packaging techniques meticulously followed by the pharmaceutical manufacturer, coupled with careful and attentive handling of the dispenser by the ultimate user, the consumer.

Although most consumers are aware of the need to maintain sterility in eye solutions, reliance on their expertise in so doing represents somewhat of a compromise, even under so-called optimum conditions.

Many of the prior art dispensers are physically cumbersome, and/or awkward to use. Where multi-piece components are employed and physical re-positioning of support arms or support sleeves is involved, the likelihood of contamination increases.

SUMMARY OF THE INVENTION

Accordingly, the above disadvantages and drawbacks of prior ophthalmic dispensers are largely obviated by the present invention which has for an object the provision of a novel and improved dispenser which is both simple in its structure and which provides a significantly improved resistance to inadvertent contamination of the dispenser and its contents by the user, by means of a unique barrier or guard structure that protects the orifice from inadvertent contact by the finger or skin of the user.

A related object of the invention is to provide an improved dispenser as above characterized, which can be readily molded in simple cavities, and mass produced in an economical fashion.

Still another object of the invention is to provide an improved dispenser of the type noted, wherein the closure cap is held captive during dispensing of the contents, to thereby minimize inadvertent contamination of the closure cap as might occur if the latter were to be momentarily placed on a supporting surface such as a sink or table, and thus experience intimate physical contact with such a surface.

Yet another object of the invention is to provide an improved dispenser as above characterized, which is easy to use, and which does not rely upon special manipulative procedures on the part of the consumer, in arriving at a safe and contamination-free administration of the desired dosage.

A still further object of the invention is to provide an improved dispenser in accordance with the foregoing, which is physically small and light weight, and wherein the guard structure that is provided does not materially interfere with normal discharge of the dispenser's contents.

The above objects are accomplished by a liquid dispenser for eye drops, antiseptic solutions and the like which are intended to be applied in the form of droplets, comprising in combination a dispenser cap having a body portion for attachment to the neck of a container in which the liquid is carried, the cap having a projecting spout provided with an orifice through which the dispensed liquid passes, and the spout having broad exterior surfaces consisting of tapered sides and a transverse end wall in which latter the orifice is disposed, and a plurality of projections on the exterior broad surfaces of the spout, adapted to intercept an exterior approaching object and to minimize the likelihood of such object coming into intimate engagement with the broad surfaces of the spout and contaminating the same.

The arrangement is such that the orifice is effectively guarded against inadvertent brushing or touching, typically by the finger of the user as he or she is opening the dispenser. Significantly reduced possibility of contamination is realized, with virtually no increase in cost over prior dispensers of the type for dispensing liquids in such droplet form, as noted above.

Other features and advantages will hereinafter appear.

BRIEF DESCRIPTION OF THE DRAWINGS

FIG. 1 is a top plan view of the dispenser cap of the invention, enlarged to about double size and illustrated in the open position of the stopper and with the cap portions oriented in the positions they occupy as they leave the mold.

FIG. 2 is a side elevational view of the cap shown in FIG. 1.

FIG. 3 is a fragmentary view of the cap still further enlarged, shown partly in side elevation and partly in vertical section with the stopper in the closed, sealing position on the dispensing spout.

FIG. 4 is an enlarged fragmentary side elevational view of the spout portion of the cap inverted, showing a drop of liquid emerging from the spout.

FIG. 5 is a top plan view of the spout portion of the dispensing cap, and

FIG. 6 is a fragmentary axial sectional view of a modification, showing a slightly shortened spout and orifice portion of a cap embodying the invention.

DESCRIPTION OF THE PREFERRED EMBODIMENT

Referring first to FIGS. 1 and 2, the improved dispensing cap of the invention is shown as comprising a single molded plastic piece in the form of a cap proper 10 and a stopper 12 therefor, connected with each other by a flexible and resilient tie or web 14. The cap proper comprises an internally threaded cap body 16 having a top wall 18 from which there rises a base portion 20 that mounts a spout 22. An annular sealing bead 24 on the spout 22 cooperates with an internal sealing bead 25 in the stopper 12 to effect a seal when the stopper is disposed on the spout 22 as seen in FIG. 3.

As is usual, the cap 10, spout 22 and stopper 12 together with the tie 14 are simultaneously molded in a suitable die, all at the same time. The tie 14 can comprise spaced-apart parallel webs or web branches 28 joined by a yoke portion 30 which connects with the stopper 12 by a single web 31.

The interior of the cap 10 communicates with a discharge passage in the spout 22. In the modification of FIG. 6, the discharge passage is indicated by the numeral 34a, and the spout 22a in this figure has a drop-sizing or measuring chamber 36a which connects the passage 34a to the spout orifice 38a.

In FIG. 4 the spout 22 is shown inverted and discharging a droplet 39 of product, from its orifice 38.

In accordance with the present invention, means are provided on the exterior surfaces of the spout 22, to minimize contamination of the spout in the event that it inadvertently comes in contact with exterior objects, as for example the user's finger as he or she pries the stopper off the cap, just prior to use, or a piece of wiping tissue that may be used to dab the eyes if the dispenser is being used as an eye dropper. Such means are in the form of projections provided on the surfaces of the spout 22, preferably projections in the form of a plurality of ribs 44.

As shown in FIGS. 1 and 5, eight ribs 44 are molded on the spout 22 at the same time that the entire cap assemblage is being molded. The ribs 44 extend over the exterior broad surfaces of the spout, namely extending radially on the end wall 46 of the spout 22, and also downward along the tapered conical sides of the spout. The ribs 44 need not be very high to accomplish the desired result of preserving sterility of the orifice and its surrounding surfaces, namely by guarding the tip against an inadvertent brushing or touching by the user's finger, or an inadvertent interception of pieces of tissue and the like, as can be understood. As seen in FIG. 3, the ribs 44 can occupy the existing space 48 between the walls of the stopper 12 and the conical exterior of the spout 22. The presence of the ribs 44 does not interfere with the formation or disposition of droplets, such as the droplet 39, from the spout; nor do the ribs 44 interfere with wiping clean of the spout exterior, if desired, as by a suitable sterile pad.

In a preferred form, the inner surface of the stopper is spaced from the uppermost surfaces of the ribs, so that physical contact between the inner surface and ribs is minimized. As a consequence, residue which may accumulate in the hollow of the stopper is normally not readily transferred to the area around the orifice, which as noted above, is intended to be maintained as clean as possible during the useful life of the dispenser.

From the above it can be seen that I have provided a novel and improved dispenser which is extremely simple in its structure, and which provides significant advantages from the standpoint of minimizing inadvertent contamination of the dispenser's contents, and of the orifice through which the contents are discharged. The extreme simplicity of the construction is attained at virtually no additional cost, since the molding of the ribs on the spout is accomplished at the same time that the spout is formed. Also, an important consideration is that no interference with normal dispensing occurs as a consequence of the presence of the ribs.

The disclosed device is thus seen to represent a distinct advance and improvement in the ophthalmic dispenser field.

Variations and modifications are possible without departing from the spirit of the invention.

Each and every one of the appended claims defines an aspect of the invention which is separate and distinct from all others, and accordingly it is intended that each claim be treated in this manner when examined in the light of the prior art devices in any determination of novelty or validity.

What is claimed is:

1. A liquid dispenser for eye drops, or antiseptic solutions which are intended to be applied in the form of droplets, comprising in combination:
   a) a dispenser cap having a body portion for attachment to the neck of a container in which the liquid is carried,
   b) said cap having a projecting spout provided with an orifice through which the dispensed liquid passes,
   c) said spout having broad exterior surfaces comprising tapered sides and a transverse end wall in which latter the orifice is disposed, and
   d) a plurality of projections directly carried on the broad exterior surfaces of the spout, said projections extending radially from the orifice on the transverse end wall, and thereafter extending down the tapered sides of the spout, and said projections also extending outwardly from said surfaces, said projections being adapted to intercept an exterior approaching object and to minimize the likelihood of such object coming into intimate engagement with the broad exterior surfaces of the spout and contaminating the same.

2. A liquid dispenser according to claim 1, wherein:
   a) said projections comprise ribs disposed at spaced intervals on the exterior surfaces of the spout.

3. A liquid dispenser according to claim 1, wherein:
   a) said projections comprise ribs disposed at spaced intervals on the tapered sides of the spout.

4. A liquid dispenser according to claim 1, wherein:
   a) said spout end wall is annular, and
   b) said projections comprise ribs disposed on said annular end wall.

5. A liquid dispenser according to claim 1, wherein:
   a) said projections comprise upstanding ribs disposed at spaced intervals on the transverse end wall of the spout, and extending downwardly on said tapered sides of the spout.

6. A liquid dispenser according to claim 1, wherein:
   a) said spout includes a drop-sizing chamber.

7. A liquid dispenser according to claim 4, wherein:
   a) said ribs are disposed radially on the annular end wall of the spout.

8. A liquid dispenser according to claim 5, wherein:
   a) said spout has a conical configuration.

9. A liquid dispenser according to claim 1, and further including:
   a) a stopper receivable on the spout, for closing off the orifice thereof.

10. A liquid dispenser according to claim 9, wherein:
    a) said stopper has an inner surface which is spaced from the broad exterior surfaces of the spout,
    b) said projections comprising multiple ribs disposed in the space between said broad exterior surfaces of the spout and said inner surface of the stopper.

11. A liquid dispenser according to claim 10, wherein:
    a) said ribs are spaced from the inner surface of the stopper when the latter is carried by the spout.

12. A liquid dispenser according to claim 9, wherein:
    a) said stopper has a finger engageable lifting edge which enables it to be pried off by the user's finger.

13. A liquid dispenser according to claim 9, and further including:
    a) a flexible web integrally formed with the body portion and stopper, and retaining the latter captive on the body portion.

14. A liquid dispenser according to claim 13, wherein:
    a) said web has a portion comprising spaced apart branches.

15. A liquid dispenser according to claim 9, wherein:
    a) said stopper has a transverse top wall with an inner surface, and
    b) said inner surface being spaced above and separated from said projections when the stopper is received on the spout.

16. A liquid dispenser according to claim 9, wherein:
    a) said projections comprise ribs on said transverse end wall,
    b) said stopper having an inner surface which is spaced above said transverse end wall when the stopper is received on the spout,
    c) said ribs being disposed in the space between the inner surface of the stopper and the transverse end wall of the spout.

17. A liquid dispenser according to claim 1, wherein:
    a) said projections at the location of the tapered sides extend outwardly from said tapered sides in radial directions.

18. A liquid dispenser according to claim 1, where in:
    a) said projections at the location of the transverse end wall extend upwardly from said end wall in an axial direction.

* * * * *